United States Patent
Levine et al.

(10) Patent No.: US 7,502,114 B2
(45) Date of Patent: Mar. 10, 2009

(54) OZONE CONCENTRATION SENSOR

(75) Inventors: Stephan Levine, Berlin (DE); Johannes Seiwert, Berlin (DE); Joachim Lohr, Berlin (DE); Ulrich Brammer, Berlin (DE); Jens Fittkau, Berlin (DE)

(73) Assignee: MKS Instruments, Inc., Wilmington, MA (US)

( * ) Notice: Subject to any disclaimer, the term of this patent is extended or adjusted under 35 U.S.C. 154(b) by 154 days.

(21) Appl. No.: 10/799,331

(22) Filed: Mar. 12, 2004

(65) Prior Publication Data

US 2005/0200848 A1    Sep. 15, 2005

(51) Int. Cl.
*G01N 21/00* (2006.01)
(52) U.S. Cl. .................................... 356/432
(58) Field of Classification Search ................ 356/407, 356/409–411, 432–442, 445–448
See application file for complete search history.

(56) References Cited

U.S. PATENT DOCUMENTS

| | | | |
|---|---|---|---|
| 2,775,160 A | 12/1956 | Foskett et al. | |
| 3,690,772 A | 9/1972 | Alfons | |
| 3,726,598 A * | 4/1973 | Gilby et al. | 356/244 |
| 3,835,322 A * | 9/1974 | Komatsu | 436/118 |
| 4,209,232 A * | 6/1980 | Chernin | 359/858 |
| 4,297,579 A * | 10/1981 | Spaeth | 250/343 |
| RE31,246 E * | 5/1983 | Adrian et al. | 250/343 |
| 4,567,366 A | 1/1986 | Shinohara et al. | |
| 4,749,640 A | 6/1988 | Tremont et al. | 430/314 |
| 5,009,493 A * | 4/1991 | Koch et al. | 359/858 |
| 5,220,402 A * | 6/1993 | Harvey | 356/246 |
| 5,370,846 A | 12/1994 | Yokomi et al. | 422/186.07 |
| 5,387,979 A * | 2/1995 | Brauer et al. | 356/435 |
| 5,776,296 A | 7/1998 | Matthews | 156/345 |
| 5,971,368 A | 10/1999 | Nelson et al. | 261/64.3 |
| 6,061,139 A * | 5/2000 | Takezawa et al. | 356/407 |
| 6,080,531 A | 6/2000 | Carter et al. | 430/329 |
| 6,388,752 B1 * | 5/2002 | Ziegler et al. | 356/436 |
| 6,585,898 B1 | 7/2003 | Ekberg et al. | |
| 6,791,689 B1 * | 9/2004 | Weckstrom | 356/437 |
| 2003/0025909 A1 * | 2/2003 | Hallstadius | 356/436 |

FOREIGN PATENT DOCUMENTS

| | | |
|---|---|---|
| DE | 4214840 A1 | 11/1993 |
| EP | 0497247 | 8/1992 |
| EP | 0567860 | 11/1993 |
| EP | 1010975 A | 6/2000 |
| WO | WO 95/02895 | 1/1995 |

* cited by examiner

*Primary Examiner*—Tarifur R. Chowdhury
*Assistant Examiner*—Isiaka O Akanbi
(74) *Attorney, Agent, or Firm*—Proskauer Rose LLP

(57) ABSTRACT

An apparatus and method provide measurement of a constituent of a fluid, such as ozone in ozonated water. The apparatus includes a vessel to contain the fluid, a light source configured to direct a first band of light and a second band of light along a substantially shared path though the fluid, and a photosensor that senses the first band of light and the second band of light. The constituent has a greater absorption associated with the first band of light than with the second band of light. The method includes modification of a measured attribute of the component in response to the sensed second band of light to improve the accuracy of the measured attribute.

37 Claims, 2 Drawing Sheets

200

(Step 210) selecting a first band of light for which a constituent of a fluid has a greater absorption than for a second band of light (Step 220) sensing the first band of light and the second band of light passing along a substantially shared path through the fluid (Step 230) modifying a measured attribute of the constituent determined from the sensed first band of light in response to the sensed second band of light to improve the accuracy of the measured attribute (Step 240) optionally causing the ozonated water to flow through a vessel from an ozonated water generator to a process tool to permit in situ measurement of the ozone concentration (Step 250) optionally alternately directing the first band of light and the second band of light along the substantially shared path (Step 260) optionally sensing at least one of the first band of light and the second band of light along at most a portion of the substantially shared path, and responsively maintaining an emitted intensity of at least one of the first band of light and the second band of light

FIG. 2

OZONE CONCENTRATION SENSOR

FIELD OF THE INVENTION

The present invention relates generally to an apparatus and methods for materials analysis. More particularly, the invention relates to measurement of ozone concentration of ozonated fluid.

BACKGROUND OF THE INVENTION

Ozone concentration in ozonated water is often measured via absorption spectroscopy. Ultraviolet (UV) and yellow-red bands of light are suitable due to a good match to ozone's absorption characteristics. The peak absorption for the UV Hartley band is about 2000 times greater than for the yellow-red Chappius band, so use of a UV source can provide greater measurement sensitivity than use of a yellow-red source. A UV source, however, can be expensive and can produce an unstable light intensity. Therefore, use of visible light can be preferred when the greatest sensitivity is not required.

Ozonated water has many industrial applications. In the semiconductor manufacturing industry, for example, accurate control of the ozone concentration of ozonated water produced by an ozonated water generator can be critical during device fabrication. Common approaches to measuring ozone concentration for such generators are often slow, prone to error, and/or inconvenient. For example, ozone concentration can be measured by collecting a sample of ozonated water from the generator and testing it with an absorption spectroscopy-based analytical device. Thus, there can be errors and delays in measurements due to sample handling. Further errors can be introduced by anomalous scattering of light as it passes through the water. Such scattering caused, for example, by bubbles, can produce light intensity losses that can be difficult to distinguish from intensity losses that are due to ozone absorption.

SUMMARY OF THE INVENTION

The invention involves an apparatus and methods that can improve measurement accuracy, ease, and cost for absorption spectroscopy of attributes of a constituent of a fluid. According to principles of the invention, measurement accuracy can be improved by correcting for intensity losses arising from effects other than constituent-absorption effects. The invention arises, in part, from the realization that anomalous absorption can be determined by observing a second radiation that travels a shared path with the first radiation and is less absorbed than the first radiation. Measurement of the intensity of the second radiation can thus be used to assess how much loss of the first radiation is due to anomalous effects, such as scattering of the radiation by bubbles in the fluid.

The invention also arises, in part, from the realization that an output pipeline of an ozonated water generator can be modified to permit full-flow real-time (or near real-time) in situ measurements of ozone concentration. As described above, two bands of light, i.e., radiation, can be directed through a portion of the output pipeline, using reflections, as desired, to increase a path length and thereby a measurement sensitivity. The bands of light have different absorption characteristics with respect to ozone; the band having lesser or no absorption due to ozone provides a reference signal. By directing the two bands of light along substantially the same path, the reference signal can be used to correct for intensity loss of the first band of light arising from factors other than absorption by ozone.

The two bands of light can be provided, for example, by a yellow-light light-emitting diode (LED) and a blue-light LED. One or more LEDs can provide a stable, low-cost source of light. Thus, ozone concentration can be measured by direct examination of the full-flow ozonated water output of a generator in real-time with improved accuracy and lower cost than some prior methods.

Accordingly, in a first aspect, the invention features an apparatus for measuring a constituent of a fluid, for example, ozone in ozonated water. The apparatus can include a vessel to contain the fluid, a light source configured to direct a first band of light and a second band of light along a substantially shared path though the fluid, and a photosensor.

The first band of light and the second band of light are selected so that the absorption by the constituent of the first band of light is greater than the absorption by the constituent of the second band of light. The second band of light provides a reference signal to permit correction of measurements derived from the first band of light.

The photosensor senses the first band of light and the second band. The photosensor can include one or more components, for example, one or more photodiodes. The photosensor supports intensity measurements of the bands of light. The measured intensity of the first band can provide a determination of an attribute of the constituent, such as the concentration of the constituent. The measured intensity of the second band can provide a reference signal to support error corrections of the attribute determinations.

For example, the fluid can be water and the constituent can be ozone. The vessel can be, for example, a portion of a ozonated water delivery pipeline. Thus the apparatus can provide in situ measurement of ozone concentration in ozonated water as it flows from an ozonated water generator. An ozonated water generator can include the vessel as a portion of the generator's ozonated water delivery pipeline. Thus, the apparatus can support real-time measurements of ozonated water produced by the generator, without requiring collection of an ozonated water sample from the generator.

The component of the photosensor has an absorption band that overlaps the first band of light. For example, for ozonated water measurements, the first band of light can be associated with a yellow-red frequency and a first width, and the second band of light can be associated with a blue frequency and a second width. The blue light is relatively unabsorbed by ozone. The light source can include one or more LEDs, for example, a GaAsP on GaP LED.

The substantially shared path can be defined in part by at least one reflection site to increase a length of the path through the fluid in the vessel, thereby increasing a measurement sensitivity for the constituent in the fluid. A vessel having a compact size can thus provide a relatively long path length.

Factors other than constituent absorption can cause a loss in intensity of the first and second bands of light passing through the fluid (such factors include, for example, bubbles in the fluid.) Thus, an observed loss of intensity of the second band of light provides an indication of a loss of intensity of the first band of light that arises from such factors. Preferably, the paths of the first and second bands of light are substantially shared so that the two bands of light pass through substantially the same fluid. Thus, the second band of light can pass through substantially the same fluid as the first band of light and/or sample substantially the same mechanical factor(s) as the first band of light.

The vessel can include transparent, translucent, and/or opaque materials. The apparatus can also include a coating adjacent to the vessel. The vessel itself can provide a reflection site. Alternatively, the coating can reflect the light. The reflection site can produce a mirror or a diffuse reflection, depending upon the selection of materials for the vessel and/or the coating.

The apparatus can include a second photosensor. The second photosensor can support, for example, detection of differential aging effects of a light source that includes two LEDs. The apparatus can also include a temperature sensor and/or a pressure sensor. Temperature and pressure measurements can support further corrections to attributes determined from intensity losses of the first band of light.

In a second aspect, the invention features a method for measuring a constituent of a fluid, according to principles of the invention. The method includes selecting a first band of light for which the constituent has a greater absorption than for a second band of light, sensing the first band of light and the second band of light passing along a substantially shared path through the fluid, and modifying a measured attribute of the constituent determined from the sensed first band of light in response to the sensed second band of light to improve the accuracy of the measured attribute.

The measured attribute of the ozone can be any attribute of interest, for example, a concentration of the ozone. The measured attribute can be modified to correct the measured concentration for errors arising from an intensity loss of the sensed first band of light associated with one or more factors other than absorption by the constituent (i.e., other than by absorption by ozone). Such intensity losses may otherwise be misinterpreted as arising from absorption by ozone, and can thus lead to a false increase in measured concentration.

Factors that may cause a decrease in intensity include, for example, bubbles, a reflectivity of a reflection site of the substantially shared path, an impurity in the fluid, and a mechanical dimension of a vessel containing the fluid. For example, a change in reflectivity and/or dimensions of the vessel can cause a decrease (or increase) in a measured intensity of the first band of light. Such a decrease (or increase) in intensity is unrelated to absorption by ozone, but can be falsely interpreted as an increase (or decrease) in absorption by ozone.

BRIEF DESCRIPTION OF THE DRAWINGS

This invention is described with particularity in the appended claims. The above and further advantages of this invention may be better understood by referring to the following description taken in conjunction with the accompanying drawings, in which:

FIG. 2 is a flowchart of an embodiment of a method for measuring a component of a fluid, according to principles of the invention.

DETAILED DESCRIPTION

Figure 1:
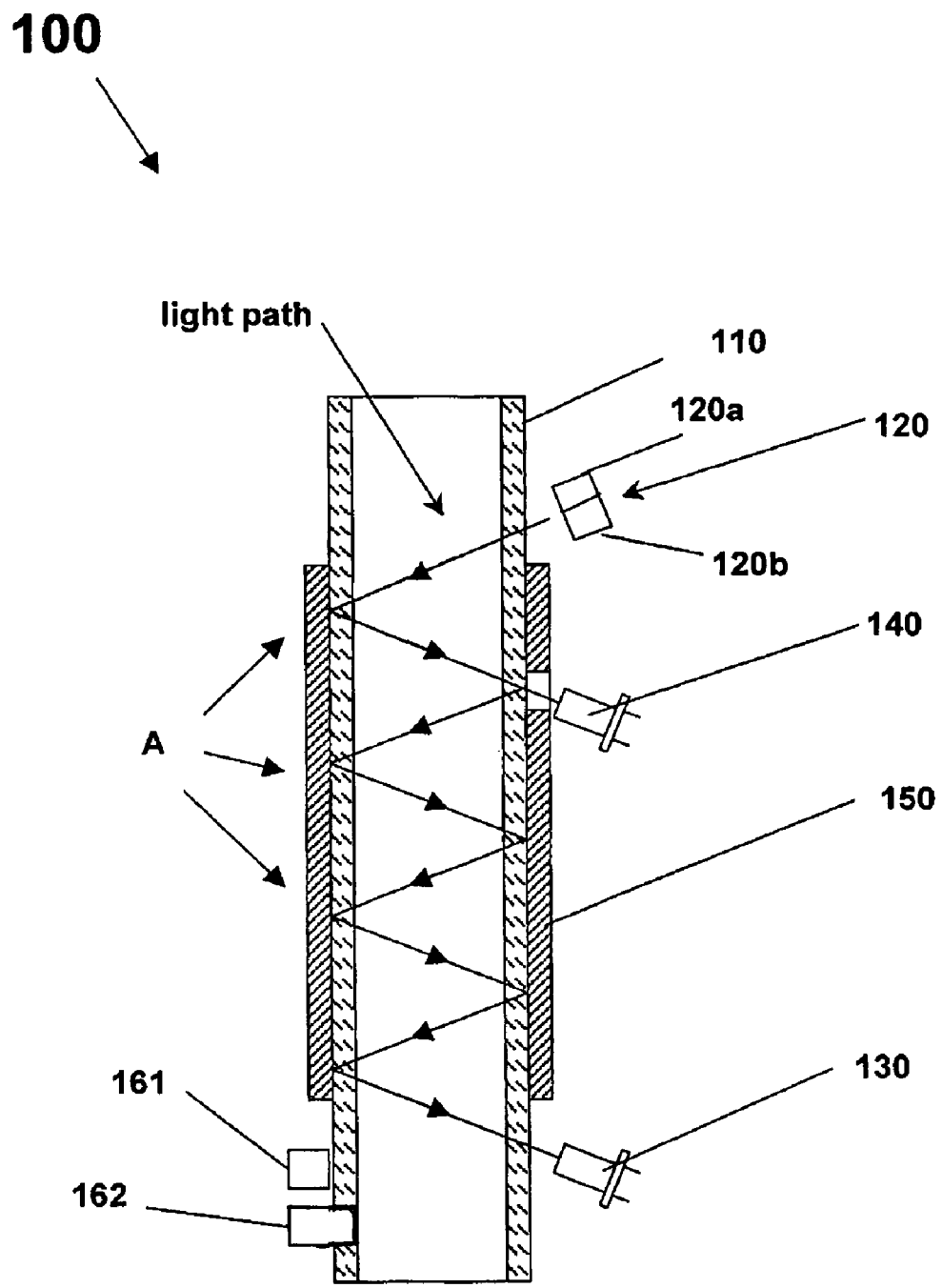
FIG. 1 is a block diagram of an embodiment of an apparatus for measuring a constituent of a fluid, according to principles of the invention.

Definitions—An "ozonated water generator" is an apparatus that produces ozonated water by introducing ozone gas into water through use of, for example, a contactor.

The term "light" refers to electromagnetic radiation, including infrared, visible, ultraviolet, and x-ray radiation. The terms "light" and "radiation" are herein used interchangeably.

A "band of light" is associated with a peak frequency and a bandwidth, for example, a half-maximum bandwidth.

A "vessel" is a container or portion of a container that can contain a fluid. A vessel can be, for example, a pipeline or a portion of a pipeline.

FIG. 1 is a diagram of a cross-section of an embodiment of an apparatus 100 for measuring a constituent of a fluid, according to principles of the invention. The apparatus includes a vessel 110 to contain the fluid, a light source 120 configured to direct a first band of light and a second band of light along a substantially shared path though the fluid in the vessel, and a photosensor 130 that senses the first band of light and the second band of light passing along the substantially shared path. The first and second bands of light from light source 120 can be transmitted sequentially or simultaneously. For example, the first band of light can be transmitted and detected by photosensor 130, and then the second band of light can be transmitted and detected by photosensor 130. In other embodiments, the first and second bands of light can be transmitted simultaneously by light source 120. Detection of these bands of light by the photosensor 130 can then be performed simultaneously. Embodiments also include sequential detection of the light bands by photosensor 130 when both are simultaneously transmitted by light source 120.

The first band of light and the second band of light are selected so that the constituent to be measured has a greater absorption for the first band of light than for the second band of light. The second band of light provides a reference signal to correct measurements derived from the first band of light.

For example, the fluid can be water and the constituent can be ozone. The vessel 110 can then be, for example, a portion of a delivery pipeline for ozonated water to permit in situ measurement of the ozone. Thus, an ozonated water generator can be modified by using the vessel 110 as a portion of a delivery pipeline of the ozonated water generator. The apparatus 100 can provide real-time, or near real-time, measurements of ozonated water produced by the generator, without requiring collection of an ozonated water sample from the generator.

The constituent to be measured has an absorption band that overlaps the first band of light. For example, for ozonated water measurements, the first band of light can be associated with a yellow-red frequency and a first width, and the second band of light can be associated with a blue frequency and a second width. The yellow-red frequency can be, for example, approximately 584 nm, and the blue frequency can be, for example, approximately 300 nm. The light source 120 can then include a yellow-red LED 120a to provide the first band of light, and a blue LED 120b to provide the second band of light.

The yellow-red LED 120a, for example, can be a GaAsP-on-GaP diode. The yellow-red peak wavelength output of such a diode is close to ozone's maximum absorption for visible light. Moreover, the associated ozone absorption band is broader than the width of the yellow-red output of the diode.

The substantially shared path can be defined in part by at least one reflection site A to increase a length of the path through the fluid in the vessel. The measurement sensitivity of the apparatus 100 can be increased by increasing the path length through the fluid.

The paths of the first and second bands of light are preferably substantially shared so that the two bands of light pass through substantially the same fluid. As further described below, an observed change in intensity of the second band of light can then provide a good indication of the effect of non-constituent-related factors that have affected the intensity of the observed first band of light.

The vessel 110 can include transparent, translucent, and/or opaque materials. Suitable materials include, for example, quartz, a resin, and/or a fluoropolymer such as polytetrafluoroethylene (PTFE) and perfluoroalkoxy (PFA). The apparatus 100 can also include a coating 150 adjacent to the vessel. The vessel 110 itself can provide a reflection site for the bands of light. Alternatively, the coating 150 can reflect the light.

The reflection site A can produce a mirror or a diffuse reflection depending on the selection of materials for the vessel and/or the coating 150. For example, a white polymer vessel 110, or a clear quartz vessel 110 with a white paper coating 150, can provide a diffuse reflection. Use of reflection sites A that produce a diffuse reflection can simplify design and manufacture of the apparatus 100 by reducing or eliminating a need to align reflection sites A of a mirror type. The vessel 110 can thus include a material that defines an inner surface of the vessel that diffusely scatters the first and second bands of light at the reflection site A. Alternatively, light may be allowed to pass through a transparent vessel and to reflect from a coating 150.

The photosensor 130 senses the first band of light and the second band of light passing along the substantially shared path. The photosensor 130 can include, for example, one or more silicon photodiodes, photo transisitors, photo-multiplier tubes, or other devices known in the art. As described below, the photosensor 130 supports intensity measurements of the bands of light. One photosensor (e.g., 130) can support more than one component. For example, a photosensor can include two components, and each component can be a photodiode. A photosensor including two photodiodes can simultaneously measure the intensities of two different light bands. The measured intensity of the first band can provide a determination of an attribute, such as concentration, of a constituent in the fluid. The measured intensity of the second band can provide a reference signal to support error corrections of the attribute determinations.

The apparatus 100 can further include a second photosensor 140. The second photosensor 140 can be positioned to sense the first band of light and the second band of light after they pass along at most a portion of the substantially shared path. The second photosensor 140 can be used to support detection of differential aging of, for example, the LEDs 120a, 120b. Thus, for example, a loss of light output from the yellow-red LED 120a due to aging can be determined, and corrected, by increasing a current supplied to the LED 120a to increase its output.

In some embodiments, the first and second bands of light from light source 120 can be transmitted sequentially or simultaneously. If they are transmitted simultaneously, then detection of either of these bands of light by the second photosensor 140 can be performed simultaneously or sequentially. For example, one band of light can be detected by photosensor 130, while the other band of light is simultaneously detected by the second photosensor 140.

Further, although only two bands of light have been described, more than two bands can be used. If more than two bands of light are transmitted by light source 120, at least one of photosensors 130, 140 can be used to simultaneously detect two (or more) light bands of interest. Sequential detection can also be performed, either simultaneously (e.g., with two photosensors) or sequentially (using one or two photosensors).

Based on this description, other suitable combinations will also become apparent to one of skill in the art. For example, other light source configurations can be used. A single light source can be used that has an adjustable light wavelength output, which can be either continuously or discretely adjustable. The light absorption of the different wavelengths could then be detected with photosensors as described above. Yet another embodiment includes multiple light sources and multiple detectors, in which each detector has a spectral sensitivity corresponding to a particular one of the light sources. Thus, a first light source (e.g., a first photodiode) transmits a first light band and is paired with a first detector, a second light source (e.g., a second photodiode) transmits a second light band and can be paired with a second detector, etc. Preferably, the light paths of the light bands from the different light sources are substantially the same. More than two light source/photosensor pairs can be used, depending upon the requirements of the measurement application. The detectors in such embodiments can be, for example, any of the types of photosensors 130 described above.

The apparatus 100 can also include at least one temperature sensor 161 and/or at least one pressure sensor 162. The temperature and pressure measurements provided by these sensors 161, 162 can support further corrections to measured attributes, which have been determined from intensity losses of the first band of light. In some applications, the results achieved can be affected by temperature and pressure. When required, compensation can be provided based on information obtained from temperature sensor 161 and/or pressure sensor 162, resulting in more precise attribute measurement results.

FIG. 2 is a flowchart of an embodiment of a method 200 for measuring a constituent of a fluid, according to principles of the invention. The method 200 may be implemented with, for example, the apparatus 100 illustrated in FIG. 1. The method 200 includes selecting a first band of light for which the constituent has a greater absorption than for a second band of light (Step 210), sensing the first band of light and the second band of light passing along a substantially shared path through the fluid (Step 220), and modifying a measured attribute of the constituent determined from the sensed first band of light in response to the sensed second band of light to improve the accuracy of the measured attribute (Step 230).

The fluid can be ozonated water as produced by, for example, an ozonated water generator. The constituent can then be ozone. The remainder of this description refers to water and ozone as examples of a fluid and a constituent of a fluid. It will be understood, however, that principles of the invention may be applied to other fluids and other constituents of fluids.

The measured attribute of the ozone can be any attribute of interest, for example, a concentration of the ozone. The step of modifying (Step 230) can then include correcting the measured concentration for errors arising from an intensity loss of the sensed first band of light associated with one or more factors other than absorption by the constituent. Such intensity losses may otherwise be misinterpreted as arising from absorption by ozone, and can thus lead to a false increase in measured concentration.

Factors that may cause a decrease in intensity include, for example, bubbles, a reduction in reflectivity of a reflection site of the substantially shared path, an impurity in the fluid, and a change in a mechanical dimension of a vessel containing the fluid. A decrease in intensity arising from such factors is unrelated to absorption by ozone, but can be falsely interpreted as an increase in absorption by ozone caused by an increase in ozone concentration. The method 200 can include causing the ozonated water to flow through a vessel from an ozonated water generator to a process tool to permit in situ measurement of the ozone concentration (Step 240).

The method 200 can also include alternately directing the first band of light and the second band of light along the substantially shared path (Step 250). In this case, the first band of light and the second band of light can then be alternately sensed. The first and second bands of light can further be alternated with a blank period during which substantially no light is directed along the substantially shared path. For example, during the blank period, the background intensity can be observed. The background intensity can arise from, for example, photosensor noise and/or light from sources other than a light intentionally directed along the shared path through the fluid.

The background intensity can increase the apparent sensed intensity of the first band of light, causing an error in a concentration measurement. The background measurement can thus permit a further correction to further improve the accuracy of ozone concentration measurements. That is, for example, the measured ozone concentration can be corrected for background intensity that may falsely decrease the apparent ozone concentration.

The method 200 can include sensing at least one of the first band of light and the second band of light along at most a portion of the substantially shared path, and responsively maintaining an emitted intensity of the first band of light in response to the second band of light. Thus, for example, as described above, differential aging effects of LED light sources can be detected. As known to one having skill in the LED arts, the light intensity output of an LED can decrease with age, for a giving input voltage. Further, different types of LEDs can exhibit different rates of aging.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. An apparatus for measuring an attribute of ozone, the apparatus comprising:
   a delivery pipeline to contain ozonated water for delivery to a semiconductor process tool, the delivery pipeline including a plurality of reflection sites;
   a light source configured to direct a first band of visible light and a second band of visible light along a substantially shared path through the ozonated water in the delivery pipeline, the first and second bands of visible light diffusely scattered by the plurality of reflection sites, wherein ozone in the ozonated water has a greater absorption associated with the first band of visible light than with the second band of visible light; and
   a photosensor that senses the first band of visible light and the second band of visible light passing along the substantially shared path for measuring the attribute of the ozone in the ozonated water.

2. The apparatus of claim 1, wherein the delivery pipeline permits in situ measurement of the ozone in the ozonated water during delivery of the ozonated water to the semiconductor process tool.

3. The apparatus of claim 1, wherein the first band of visible light is associated with a yellow-red frequency and a first width, and the second band of visible light is associated with a blue frequency and a second width.

4. The apparatus of claim 3, wherein the light source comprises a yellow-red light-emitting diode to provide the first band of visible light, and a blue light-emitting diode to provide the second band of visible light.

5. The apparatus of claim 4, further comprising a second photosensor that senses the first band of visible light and the second band of visible light after they pass along at most a portion of the substantially shared path to detect differential aging of the light-emitting diodes.

6. The apparatus of claim 1, wherein the substantially shared path is defined in part by the plurality of reflection sites to increase a length of the path through the ozonated water in the delivery pipeline, thereby increasing a measurement sensitivity for the attribute of the ozone in the ozonated water.

7. The apparatus of claim 1, wherein the delivery pipeline comprises a material that defines an inner surface of the delivery pipeline for diffusely scattering the first and second bands of visible light at the plurality of reflection sites.

8. The apparatus of claim 1, further comprising a coating on an exterior surface of the delivery pipeline for diffusely scattering the first and second bands of visible light at the plurality of reflection sites.

9. The apparatus of claim 1, wherein the attribute of the ozone in the ozonated water has an absorption band that overlaps the first band of visible light.

10. The apparatus of claim 1, wherein the light source comprises a light-emitting diode.

11. The apparatus of claim 1, wherein the delivery pipeline comprises a material selected from the group of quartz and a polymer.

12. The apparatus of claim 1, wherein the photosensor senses the first band of visible light and the second band of visible light after the first band of visible light and the second band of visible light pass along the substantially shared path.

13. The apparatus of claim 1, wherein the photosensor senses the first band of visible light and the second band of visible light as the first band of visible light and the second band of visible light pass along a portion of the substantially shared path.

14. The apparatus of claim 1, further comprising a temperature sensor, for measuring a temperature of the ozonated water in the delivery pipeline.

15. The apparatus of claim 1 wherein the attribute is ozone concentration.

16. The apparatus of claim 1 wherein the attribute is absorption of the first or second bands of visible light by the ozone.

17. The apparatus of claim 1, wherein the plurality of reflection sites affects an amount of diffuse scattering of the first or second bands of visible light.

18. The apparatus of claim 1, wherein the photosensor is positioned along the substantially shared path for sensing the first and second bands of visible light as the first and second bands of visible light pass through the delivery pipeline.

19. The apparatus of claim 1, further comprising a second photosensor positioned along a longitudinal axis defined by an external surface of the delivery pipeline for sensing the first band of visible light and the second band of visible light passing along the substantially shared path prior to the first and second bands of visible light reaching the photosensor.

20. The apparatus of claim 1, wherein an interior surface of the delivery pipeline or an exterior surface of the delivery pipeline comprises a material to facilitate diffuse scattering of the first or second bands of visible light.

21. The apparatus of claim 20, wherein the material is a coating.

22. The apparatus of claim 1, wherein the plurality of reflection sites facilitates a diffuse reflection by the first and second bands of visible light within the delivery pipeline.

23. An ozonated water generator, comprising:
   a contactor for mixing water and ozone gas to produce ozonated water;
   a delivery pipeline in fluid communication with the contactor for delivery of ozonated water to a semiconductor process tool, the delivery pipeline including a plurality of reflection sites;

a light source configured to direct a first band of visible light and a second band of visible light along a substantially shared path though the ozonated water in the delivery pipeline, the first and second bands of visible light diffusely scattered at the plurality of reflection sites in the delivery pipeline, wherein ozone in the ozonated water has a greater absorption associated with the first band of visible light than with the second band of visible light; and a photosensor that senses the first band of visible light and the second band of visible light after they pass along the substantially shared path for measuring an attribute of the ozone in the ozonated water.

24. A method for measuring an attribute of ozone in an ozonated water, the method comprising:

selecting a first band of visible light for which ozone has a greater absorption than for a second band of visible light;

directing the first and second bands of visible light thru a delivery pipeline to diffusely scatter the first and second bands of light at a plurality of reflection sites of the delivery pipeline;

sensing the first band of visible light and the second band of visible light after they pass along a substantially shared path through the ozonated water; and modifying a measured attribute of the ozone in the ozonated water determined from the sensed first band of visible light in response to the sensed second band of visible light to improve the accuracy of the measured attribute.

25. The method of claim 24, wherein modifying comprises correcting the measured attribute for an intensity loss of the sensed first band of visible light associated with at least one factor other than absorption by the attribute of the ozone in the ozonated water.

26. The method of claim 25, wherein the at least one factor comprises at least one of bubbles, a reflectivity of a reflection site of the substantially shared path, an impurity in the ozonated water, and a mechanical dimension of delivery pipeline containing the ozonated water.

27. The method of claim 24, further comprising providing the substantially shared path in the delivery pipeline defined at least in part by the first and second bands of visible light being diffusely reflected at the plurality of reflection sites.

28. The method of claim 27, wherein the plurality of reflection sites increase a length of the substantially shared path in the delivery pipeline.

29. The method of claim 27, further comprising causing the ozonated water to flow through the delivery pipeline from an ozonated water generator to a semiconductor process tool to permit in situ measurement of the ozone concentration in the delivery pipeline.

30. The method of claim 29, wherein alternately directing further comprises alternately directing no light along the substantially shared path.

31. The method of claim 29, further comprising sensing at least one of the first band of visible light and the second band of visible light along after the first and second bands of visible light have passed at most a portion of the substantially shared path, and responsively maintaining an emitted intensity of at least one of the first band of visible light and the second band of visible light.

32. The method of claim 24, further comprising alternately directing the first band of visible light and the second band of visible light along the substantially shared path, wherein sensing comprises alternately sensing the first band of visible light and the second band of visible light.

33. A method for producing ozonated water having a desired ozone concentration, the method comprising:

selecting a first band of visible light for which the ozone has a greater absorption than for a second band of visible light;

generating ozonated water in a ozonated water generation device;

sensing the first band of visible light and the second band of visible light after the first and second bands of visible light are diffusely scattered at a plurality of reflection sites and pass along a substantially shared path defined in part by diffuse scattering at the plurality of reflection sites through the ozonated water after the ozonated water flows from the ozonated water generation device towards a semiconductor process tool;

modifying a measured ozone concentration determined from the sensed first band of visible light in response to the sensed second band of visible light to improve the accuracy of the measured ozone concentration; and adjusting at least one parameter of the ozone water generation device until the measured ozone concentration of the ozonated water substantially matches the desired ozone concentration.

34. An apparatus for measuring an attribute of an ozonated water, the apparatus comprising:

a delivery pipeline to contain the ozonated water, the delivery pipeline defining a first end, a second end, a plurality of reflection sites, an interior surface, and an exterior surface, the interior surface and the exterior surface extending from the first end to the second end;

a light source to direct a first band of visible light and a second band of visible light along a substantially shared path through the delivery pipeline defined in part by the plurality of reflection sites, wherein ozone in the ozonated water has a greater absorption associated with the first band of visible light than with the second band of visible light and the interior surface or the exterior surface facilitates diffuse scattering of the first and second bands of visible light at the plurality of reflection sites and;

a photosensor positioned relative to the interior surface or exterior surface of the delivery pipeline for sensing the first and second bands of visible light passing along the substantially shared path to measure the attribute of the ozonated water.

35. The apparatus of claim 34, wherein the plurality of reflection sites increases a length of the substantially shared path relative to a length of the interior surface or exterior surface of the delivery pipeline.

36. An apparatus for measuring an attribute of ozone, the apparatus comprising:

a delivery pipeline to carry ozonated water from an ozonated water generator to a semiconductor process tool;

a light source configured to direct a first band of visible light and a second band of visible light through the ozonated water in the delivery pipeline, wherein ozone in the ozonated water has a greater absorption with the first band of visible light than with the second band of visible light; and a photosensor that senses the first band of visible light and the second band of visible light passing along a path for measuring an attribute of the ozone in the ozonated water.

37. The apparatus of claim 36, wherein the delivery pipeline permits in situ measurement of an attribute of ozone in the ozonated water during delivery of the ozonated water to the semiconductor process tool.

* * * * *